United States Patent [19]

Bellavia et al.

[11] Patent Number: 4,710,127

[45] Date of Patent: Dec. 1, 1987

[54] METHOD AND DEVICE FOR ESTABLISHING NEW DENTAL OCCLUSAL SCHEME FOR PATIENT

[75] Inventors: William D. Bellavia, Medina, N.Y.; William Missert, 120 Halstead St., Rochester, N.Y. 14610

[73] Assignee: William Missert, Rochester, N.Y.

[21] Appl. No.: 878,637

[22] Filed: Jun. 26, 1986

Related U.S. Application Data

[63] Continuation of Ser. No. 613,887, May 24, 1984, abandoned.

[51] Int. Cl.$^4$ ............................................. A61C 5/00
[52] U.S. Cl. ................................... 433/215; 433/218; 433/223
[58] Field of Search ................ 433/1, 215, 217.1, 218, 433/219, 223

[56] References Cited

U.S. PATENT DOCUMENTS

| | | | |
|---|---|---|---|
| 3,120,704 | 2/1964 | Newcomb | 433/1 |
| 3,468,028 | 9/1969 | Sunter | 433/218 |
| 3,530,582 | 9/1970 | Weissman | 433/219 |
| 3,763,564 | 10/1973 | Petrelli et al. | 433/217.1 |
| 4,264,308 | 4/1981 | Tanaka | 433/223 |
| 4,384,854 | 5/1983 | Garfinkel | 433/215 |
| 4,416,626 | 11/1983 | Bellavia | 433/7 |
| 4,443,197 | 4/1984 | Fusayama et al. | 433/217.1 |
| 4,557,692 | 12/1985 | Chorbajian | 433/215 |

*Primary Examiner*—John J. Wilson
*Attorney, Agent, or Firm*—Joseph P. Gastel

[57] ABSTRACT

A method of establishing a new dental occlusal scheme for a person who has vertical gaps between upper and lower teeth including the steps of making casts of the person's upper and lower teeth, building up overlay material over the cast of the lower teeth, positioning the cast of the upper teeth in articulated position relative to the cast of the lower teeth to produce a desired occlusal relationship between the cast of the upper teeth and the overlay material, curing the overlay material to produce a cured overlay, sculpting the cured overlay to produce an overlay unit consisting of a plurality of cap members resembling upper portions of crowns of natural teeth connected by struts with the cap members having the desired occlusal scheme and morphology, bonding the overlay unit to the lower teeth, severing the struts after the overlay unit has been bonded to the lower teeth to provide complete divisions between adjacent cap members, and shaping the individual cap members to merge into the natural teeth on which they are mounted. An overlay unit for bonding to a plurality of teeth to provide a new dental occlusal scheme including a plurality of individual cap members resembling upper portions of tooth crowns, lower surfaces on each of the individual cap members for complementary mating engagement with the crown portions of natural teeth on which they are to be mounted, the cap members being sculpted to have a desired occlusal scheme and morphology, and struts connecting the individual cap members to each other.

21 Claims, 6 Drawing Figures

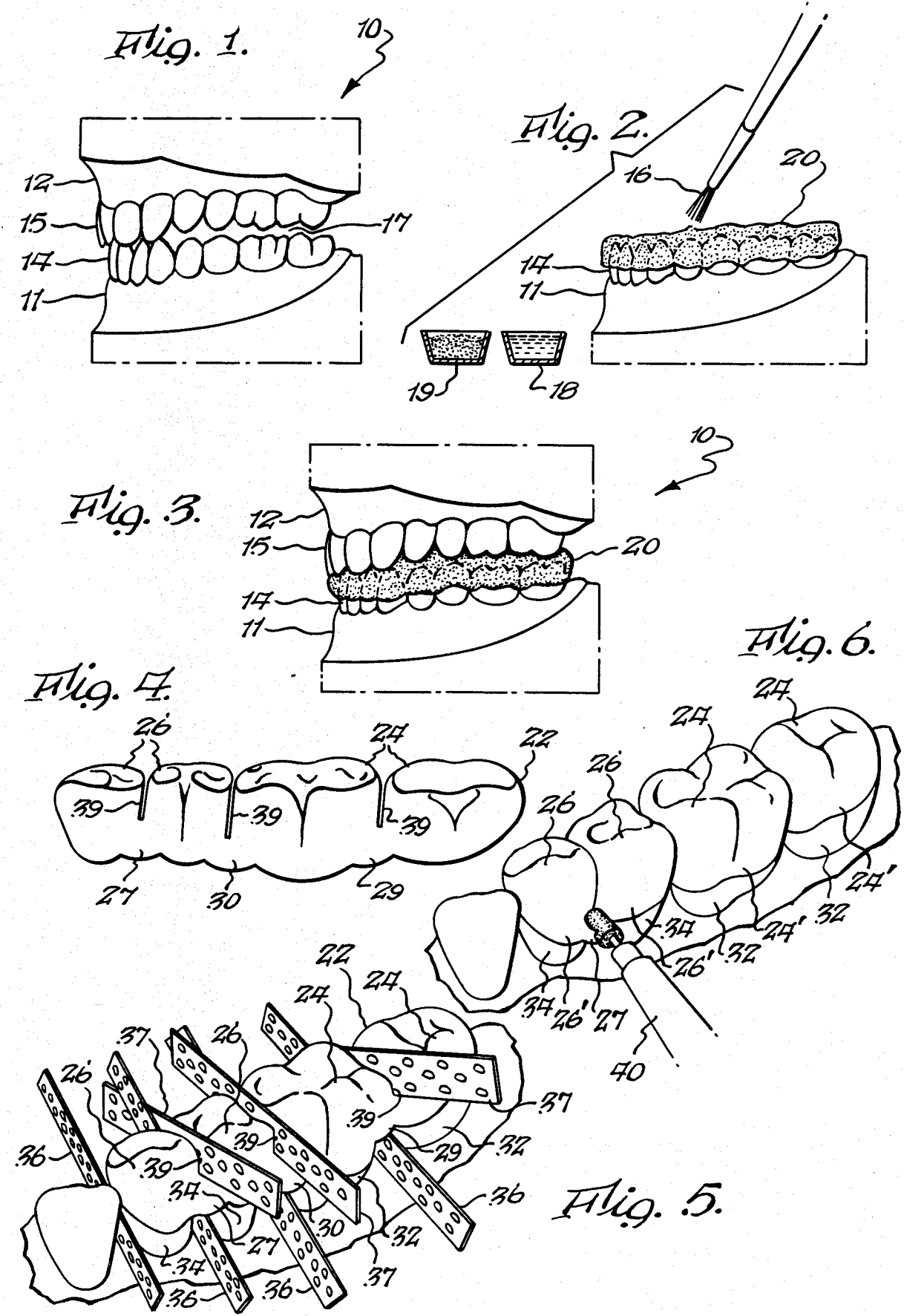

METHOD AND DEVICE FOR ESTABLISHING NEW DENTAL OCCLUSAL SCHEME FOR PATIENT

This is a continuation, division, of application Ser. No. 613,887 filed May 24, 1984, now abandoned.

BACKGROUND OF THE INVENTION

The present invention relates to a method and device for reforming the upper portions of teeth to provide a patient with an improved dental occlusal scheme and proper tooth morphology.

By way of background, in U.S. Pat. No. 4,416,626 there is disclosed a method and an orthopedic device for recapturing an anterior displaced mandibular disc by moving the mandible anteriorly from its previous position. When this method is completed, there will be a greater vertical height between the person's molars and possibly also between other teeth, so that they do not meet. In certain other situations also, as where an adult still has deciduous teeth, there also is a vertical spacing between the upper and lower teeth so that they do not meet.

SUMMARY OF THE INVENTION

It is one object of the present invention to provide a method for filling the vertical gap between upper and lower teeth to provide a desired dental occlusal scheme and proper tooth morphology.

Another object of the present invention is to provide a prosthetic device which can be applied to a person's teeth in a precise manner to provide a desired dental occlusal scheme and proper tooth morphology which permits normal flossing of natural teeth. Other objects and attendant advantages of the present invention will readily be perceived hereafter.

The present invention relates to a method of establishing a new dental occlusal scheme comprising the steps of making casts of a person's natural upper and lower teeth, constructing a build-up of material over one cast, positioning the other cast in articulated position relative to said one cast to produce a desired occlusal scheme relationship of said material with said other cast, making an overlay unit using said build-up of material as a basis, said overlay unit resembling a plurality of overlay cap members resembling outer portions of crowns of natural teeth connected by struts with said cap members having the desired occlusal scheme and morphology, bonding said overlay unit to, the persons teeth for which said build-up was made, severing said struts after said overlay unit has been bonded to said teeth to provide complete divisions between adjacent cap members which merge into the divisions between said person's teeth on which said cap members are mounted, and shaping said individual cap members to merge into the natural teeth on which they are mounted.

The present invention also relates to an overlay for bonding to a plurality of teeth to provide a new dental occlusal scheme comprising a plurality of individual cap members resembling outer portions of tooth crowns, surfaces on each of said individual cap members for complementary mating engagement with the crown portions of natural teeth on which they are to be mounted, said cap members being sculpted to have a desired occlusal scheme and morphology, and struts connecting said individual cap members to each other.

The various aspects of the present invention will be more fully understood when the following portions of the specification are read in conjunction with the accompanying drawings wherein;

BRIEF DESCRIPTION OF THE DRAWINGS

FIG. 1 is a side elevational view of models of a person's upper and lower teeth which have an orientation with a vertical spacing between the molars, as is realized when the mandible is moved anteriorly from its normal position;

FIG. 2 is a side elevational view of a person's lower teeth being covered with plastic overlay material;

FIG. 3 is a side elevational view of the model of the upper teeth being pressed onto the plastic overlay material while it is still pliable;

FIG. 4 is a perspective view of a portion of the overlay material after it has been removed from the model of the lower teeth and has been sculpted to produce an overlay unit consisting of a plurality of cap members resembling a plurality of outer portions of crowns of natural teeth connected by struts with the cap members having a desired occlusal scheme and morphology;

FIG. 5 is a fragmentary perspective view showing the overlay unit in the process of being cemented onto the crowns of a person's natural teeth while the cap members of the overlay unit are connected by struts; and FIG. 6 is a fragmentary perspective view showing the overlay unit mounted on the person's natural teeth with the connecting struts between the upper crown portions severed and also showing the cap members being shaped to merge into the person's natural teeth.

DESCRIPTION OF THE PREFERRED EMBODIMENTS

By way of background, in U.S. Pat. No. 4,416,626, a method and orthopedic device are disclosed for recapturing an anteriorly displaced mandibular disc. In this process, as explained in the patent, the mandible ultimately is established in a more anterior position than it was originally. This creates a greater vertical spacing between the molars, bicuspids and possibly also other teeth. In U.S. Pat. No. 4,416,626, the mandible was retained in its desired position by an orthopedic device to permit the molars to erupt to the point where they filled in the vertical space which was created. In contrast to this, the present invention is for providing effective contact between the upper and lower teeth without requiring eruption, with the teeth being in a desired optimum occlusal scheme, which would not necessarily follow if they were allowed to erupt.

Summarizing the present invention in advance, a process is disclosed for building up the teeth, which may include not only the molars and bicuspids, but also the cuspids and incisors to fill in the vertical spacing which was created as a result of the anterior displacement of the mandible. The buildup or overlay which is in its initial stage, consists of a unit comprising a plurality of individual cap members in the shape of the outer portions of crowns of teeth which are connected to each other by struts. The connected individual cap members are sculpted to provide the desired occlusal scheme and morphology. The overlay unit is then bonded to the tops of the lower teeth with a conventional acid etch system known in the art. Thereafter, the connecting struts are severed and each individual cap member is feather edged to merge gradually into its associated underlying supporting tooth. The fact that each upper cap member is completely separate and independent from adjacent cap members, permits the supporting teeth to be flossed in the normal manner because dental floss can be inserted between the cap members and carried downwardly into the spaces between the natural teeth.

In FIG. 1 a cast 10 is shown which includes a cast 11 of a person's lower teeth and a cast 12 of the person's upper teeth which are positioned relative to each other in the desired position, which is usually anterior of their once-used position. The casts 11 and 12 are made by the conventional manner which may be by the use of reversible or irreversible hydrocolloid materials or other impression materials placed in a tray to make a negative impression from which the positive casts are made, as is well known in the art.

Thereafter, casts 11 and 12 are mounted on an adjustable articulator which can reproduce articulator movements and they are painted with a separator material, such as sodium alginate or an oil based medium. Thereafter, the overlay is built up. More specifically, a dish 18 of monomer methyl methacrytate with quartz filler is provided along with a dish 19 of methyl methacrilate polymer, and a brush 16 is dipped alternately into the contents of dishes 18 and 19, and the resulting mixture is applied to teeth 14 until an overlay 20 of the desired height and contour is built up. A suitable overlay material is commercially known as the MYERSON CROWN AND BRIDGE MATERIAL. Other like products may also be used. This height and contour is dictated by the opposing teeth on the opposite cast when both casts are articulated, as shown in FIG. 3 wherein the overlay material does not extend above the lowermost surfaces of the upper teeth. The resulting assembly is then cured at 265° F. under 95 psi pressure for one-half hour to harden the overlay 20.

After the overlay 20 has been cured so that it forms a solid plastic mass which resembles tooth material, the casts 11 and 12 are separated and the overlay 20 is removed from the lower teeth 11. It will be appreciated that the undersurface of build-up 20 is of complementary mating configuration to the natural teeth for which it was constructed. The overlay 20 is made over all the teeth 14 of the lower jaw. However, in most instances it is only necessary to provide an overlay for the two molars on each side of the lower jaw and the two bicuspids on each side, although the overlay can be applied to all of the teeth. However, since it is only the molars and bicuspids which will generally be overlayed, the specific detailed description will be directed to this area. The foregoing description has referred to composite plastic material which is most popular at this time. However, it will be appreciated that castable glass or porcelain powders may also be used in accordance the fabrication techniques required for such materials. In this respect, when the overlay is made of castable glass, an overlay is first made of wax, a mold is then made from the wax overlay, and the glass is molded in the mold to produce the glass overlay. Thereafter, the glass overlay is sculpted as described above to produce an overlay unit. A porcelain overlay can be made in the same manner as the glass overlay, or by proper techniques it can be built up directly in the same manner as the composite plastic overlay.

In FIG. 4 an overlay unit 22 is shown which is actually a part of overlay 20 but which essentially includes crown-like portions or cap members 24 for the outer portions of the molars 32 and crown-like portions or cap members 26 for the outer portions of the biscuspids 34 on one side of the jaw, with the cap members 26 being connected by a flange or strut 27 and with the cap members 24 being connected by a strut or flange 29 and with the cap members for the adjacent bicuspid 26 and molar 24 being connected by a flange or strut 30. The overlay unit 22, as shown in FIG. 4, has the impressions of the upper teeth and is shaped by the use of proper sculpting tools, such as various types of dental burrs to provide the desired occlusal scheme and morphology, that is, the overlay unit 22 is fabricated to look like a series of interconnected cap members resembling outer portions or crowns of teeth connected by struts 27, 29 and 30. The cap members cover the side portions of the upper portions of the lower teeth on which they are mounted. They cannot cover the portions of the lower teeth which are facing each other.

Because the cap members 24 and 26 are still interconnected, they can be mounted on the natural molars 32 and bicuspids 34 (FIG. 5) and they will be oriented in proper position relative to both the lower teeth 14 and upper teeth 15, whereas it would have been extremely difficult to orient individual crown-like portions on individual teeth, were they not connected to each other. Before overlay unit 22 is mounted to the position shown in FIG. 5, conventional scalers 36 are positioned between adjacent natural lower teeth, and scalers 37 are positioned in the formed spaces 39 between the adjacent teeth of overlay unit 22. A self-curing composite bonding agent is then applied to both the concave surface of overlay unit 22 and the outer surfaces of natural teeth 32 and 34 after the natural teeth have been acid etched to increase their surface area by an acid solution and technique well-known in the art. A bonding agent which has been found suitable is commercially obtainable under the trademark MAR-BOND manufactured by Great Lakes Orthodontic Laboratories, Inc. Other bonding agents may also be used. Thereafter, the overlay unit 22 is placed into position and after the self-curing composite bonding agent hardens, the overlay unit 22 will be bonded to and become an integral part of teeth 32 and 34. The scalers 36 and 37 are then moved back and forth and removed from between the natural teeth and from the spaces 39 of unit 22. The function of the scalers is to prevent the bonding agent from entering the interdental spaces between the natural teeth and from entering crevices 39.

After the scalers 36 and 37 have been removed, the struts 27, 29 and 30 are removed by means of a tool, such as a dental burr 40, and the lower portions 26' and 24' of the crown-like cap members 26 and 24, respectively, are shaped to merge gradually into the lower teeth 34 and 32, respectively. Thus, each natural tooth, as discussed above, has a cap member which resembles the outer portion of a tooth crown and which is bonded to the natural tooth and which becomes the dictate of the overall occlusal scheme possessing the required tooth morphology.

While the foregoing description has described the process with respect to one side of the jaw, it will be appreciated that an overlay unit is also made for the other side of the jaw.

As noted above, in most instances it will be sufficient to cap only the molars and bicuspids on each side of the jaw to fill in the vertical spacing 17 between the lower teeth 14 and the upper teeth 15. However, in certain instances it may be necessary to extend the overlaying process of the individual overlay caps to the cuspids and possibly even to the lateral and central incisors. In cases where this is necessary, the above-described process is extended. Preferably, the method to be followed would be to have two overlay units covering the posterior four or five teeth on each side, as described above, and a single overlay unit covering the six teeth which include the two cuspids and four incisors. Alternately, an overlay unit for all of the normally present teeth may be installed at once and thereafter the struts or flashing between the teeth can be removed by the use of dental cutting tools, and the overlay cap members can thereafter be shaped to merge into their underlying supporting teeth. The natural teeth can be flossed in the normal manner because of the fact that the cap of each tooth is fully separate and distinct from the caps of adjacent teeth.

In certain instances where a vertical spacing 17 between the upper and lower teeth is too great, overlay caps cannot be applied to the lower teeth only because the crown-to-root ratio would be too great and thus there could eventually be damage to the supporting structures, such as tissue and bone which support and hold these teeth. In a case of this type, the following method is used. An overlay device is made on the upper teeth utilizing one half of the vertical gap to be closed in normal tooth morphology. The lingual (tongue) surface and incisal surface of the upper anterior teeth may also be overlayed. When the upper overlays are completed, the lower teeth are done in the manner as described before generating a desired occlusal scheme utilizing accepted tooth morphology.

The foregoing process is not limited to situations where a mandible has been moved anteriorly from its normal position for the purpose of recapturing a mandibular disc, but the process can also be used in situations where deciduous teeth of an adult have to be extended to have the necessary relative height with respect to adjacent adult teeth. In the foregoing respect, it will be appreciated that certain adults do not loose their deciduous (baby) teeth, and thus caps made according to the present invention can effectively extend such deciduous teeth to provide the desired occlusal scheme and morphology.

It will also be appreciated that the present prosthetic procedure can also be followed in situations where for any reason whatsoever the vertical gap between upper and lower teeth has to be filled in to improve the occlusal scheme and provide the required morphology.

While preferred embodiments of the present invention have been disclosed, it will be appreciated that it is not limited thereto but may be otherwise embodied within the scope of the following claims.

What is claimed is:

1. A method of establishing a new dental occlusal scheme comprising the steps of making casts of a person's upper and lower natural teeth, constructing a build-up of material over one cast, positioning the other cast in articulated position relative to said one cast to produce a desired occlusal scheme relationship of said material with said other cast, making an overlay device from said material, sculpting said overlay device to produce an overlay unit resembling a plurality of overlay cap members resembling outer portions of crowns of natural teeth connected by struts with said cap members having the desired occlusal scheme and morphology, bonding said overlay unit to said person's natural teeth, severing and removing said struts after said overlay unit has been bonded to said person's natural teeth to provide complete divisions between adjacent cap members which merge into the divisions between said person's natural teeth on which said cap members are mounted, and shaping said individual cap members to merge into the person's natural teeth on which they are mounted.

2. A method as set forth in claim 1 including the step of placing first scalers between the person's natural teeth underlying said overlay unit and placing second scalers between said overlay cap members of said overlay unit, said placement of said first and second scalers being prior to said step of bonding said overlay unit to said person's natural teeth to prevent said bonding agent from said bonding said person's step from bonding adjacent natural teeth to each other and from bonding said adjacent overlay cap members to each other.

3. A method as set forth in claim 1 including the step of applying a separator material to said one cast prior to building up said overlay material thereon.

4. A method as set forth in claim 1 wherein said step of constructing said build up of material is on the cast of said lower teeth.

5. A method as set forth in claim 1 wherein a plurality of overlay units are produced from said overlay device, and wherein each of said plurality of units are thereafter treated in the same manner as said overlay unit.

6. A method as set forth in claim 1 including the step of curing said overlay device prior to said sculpting step.

7. A method as set forth in claim 1 wherein said overlay device is made directly from said material on said one cast.

8. A method as set forth in claim 1 wherein said material is wax, making a mold of said wax material, and casting said overlay device in said mold.

9. A method of establishing a new dental occlusal scheme comprising the steps of making casts of a person's natural upper and lower teeth, positioning one of said casts in articulated position relative to the other of said casts, building up first material over a plurality of teeth of said one cast to a height which is a portion of the vertical gap between the teeth of said upper and lower casts, making a first overlay device from said first material, building up second material over a plurality of teeth of said other cast, placing said upper and lower casts in articulated position relative to each other so that said first overlay device forms the desired occlusal scheme with said second material, making a second overlay device from said second material, sculpting said first and second overlay devices to produce first and second overlay units each comprising a plurality of cap members resembling a plurality of outer portions of crowns of natural teeth connected by struts with said cap members having the desired occlusal scheme and morphology, bonding said first and second overlay units to the natural upper and lower teeth of said person, severing said struts of said upper and lower overlay units to provide complete division between adjacent cap members with said divisions merging into the divisions between said person's natural teeth, and shaping said individual cap members to merge into the person's natural teeth on which they are mounted.

10. An overlay structure for bonding to a person's plurality of natural teeth to provide a new dental occlusal scheme comprising a plurality of individual cap members resembling outer portions of tooth crowns, and surfaces on each of said individual cap members for complementary mating engagement with the crown portions of the person's unaltered natural teeth on which they are to be mounted, said cap members being sculpted to have a desired occlusal scheme and morphology which differs from the person's plurality of natural teeth, and permanently removable struts connecting said individual cap members to each other.

11. A method of establishing a new dental occlusal scheme comprising the steps of making casts of a person's natural upper and lower teeth, constructing a build-up of material over one cast, positioning the other cast in articulated position relative to said one cast to produce a desired occlusal scheme relationship of said material with said other cast, making an overlay unit using said build-up of material as a basis, said overlay unit resembling a plurality of overlay cap members resembling outer portions of crowns of natural teeth connected by struts with said cap members having the desired occlusal scheme and morphology, bonding said overlay unit to said person's natural teeth, severing and removing said struts after said overlay unit has been bonded to said person's natural teeth to provide complete divisions between adjacent cap members which merge into the divisions between said person's teeth on which said cap members are mounted, and shaping said individual cap members to merge into the person's natural teeth on which they are mounted.

12. A method as set forth in claim 11 wherein said overlay unit is made directly from said material on said one cast.

13. A method as set forth in claim 11 wherein said material is wax, and wherein said making of said overlay unit comprises making a mold of said wax material, casting an overlay device in said mold, and sculpting said overlay device to produce said overlay unit.

14. In a procedure wherein an anteriorly displaced mandibular disc has been recaptured by moving the mandible anteriorly with a resulting increase in the gap between certain posterior teeth, a method of establishing a new dental occlusal scheme comprising the steps of making casts of a person's upper and lower teeth, constructing a build-up of material over one of said casts, positioning the other of said casts in an articulated position relative to said one of said casts to produce a desired occlusal scheme relationship of said build-up of material with said other of said casts, sculpting a plurality of cap members for said certain posterior teeth from said build-up of material with each of said cap members having the desired occlusal scheme and morphology and resembling outer portions of crowns of natural teeth, and bonding said plurality of cap members to said certain posterior teeth to close said gap which was established by said anterior movement of said mandible, with said cap members being separated from each other in their bonded positions to permit access to the interdental spaces between adjacent posterior teeth on which they are bonded.

15. In a procedure as set forth in claim 14 wherein said build-up of material after sculpting comprises a plurality of interconnected cap members prior to said bonding step, and severing said plurality of cap members into individual caps after said bonding step.

16. In a procedure as set forth in claim 14 including the step of shaping said plurality of cap members to merge into the natural teeth on which they are bonded after said bonding step.

17. In a procedure as set forth in claim 14 including the step of sculpting a plurality of additional cap members for certain anterior teeth from said build-up of material with each of said additional cap members having the desired occlusal scheme and morphology and resembling outer portions of crowns of natural teeth, and bonding said plurality of additional cap members to said certain anterior teeth to close a gap between opposing anterior teeth which was produced by said anterior movement of said mandible with said additional cap members being separate from each other in their bonded positions to permit access to the interdental spaces between adjacent anterior teeth on which said additional caps are bonded.

18. An overlay cap structure for adding a new shape to the outer top portion of an unaltered natural tooth located above the exposed central portion thereof comprising an overlay cap including an internal surface of complementary mating shape to said outer top portion of said unaltered natural tooth on which it is to be mounted, upper portions on said cap shaped to produce a new desired occlusal scheme and morphology which differs from the occlusal scheme and morphology of said outer top portion of said unaltered natural tooth on which it is to be mounted, and lower portions on said overlay cap shaped to merge into said exposed central portion of the unaltered natural tooth on which it is to be mounted.

19. An overlay cap structure for adding new shapes to the outer top portions of first and second adjacent unaltered natural teeth located above the exposed central portions thereof for altering a person's occlusal scheme and morphology comprising first and second overlay cap members including first and second internal surfaces, respectively, of complementary mating shape to said outer top portions of said first and second unaltered natural teeth, respectively, on which they are to be mounted, upper portions on said first and second overlay caps shaped to produce a new desired occlusal scheme and morphology which differ from the occlusal scheme and morphology of said person's unaltered natural teeth on which they are to be mounted, and lower portions on said first and second caps shaped to merge into said exposed central portions of said first and second teeth on which they are to be mounted, said first and second overlay cap members being completely separate and independent of each other to permit access to the interdental space between said first and second teeth by a member passing downwardly through a space between said first and second overlay cap members.

20. A method of establishing a new dental occlusal scheme comprising the steps of making casts of a person's unaltered upper and lower natural teeth, constructing a build-up of material over one cast, positioning the other cast in articulated position relative to said one cast to produce a desired occlusal scheme relationship of said material with said other cast which differs from the person's natural occlusal scheme, making an overlay structure using said build-up of material as a basis, said overlay structure resembling a plurality of overlay cap members each resembling an outer portion of a crown of a natural tooth with each of said cap members producing a new desired occlusal scheme and morphology which differs from the person's natural occlusal scheme and morphology, bonding said overlay cap members to said person's unaltered teeth with spaces therebetween to permit access through said spaces to the interdental spaces between the person's adjacent natural teeth on which said cap members are bonded, and shaping each of said individual cap members to merge into the person's natural teeth on which they are mounted.

21. A method of establishing a new dental occlusal scheme comprising the steps of making casts of a person's upper and lower unaltered natural teeth, constructing a build-up of material over one cast, positioning the other cast in articulated position relative to said one cast to produce a desired occlusal scheme relationship of said material with said other cast which is different from the person's natural occlusal scheme, making an overlay structure using said build-up of material as a basis, said overlay stucture resembling a plurality of overlay cap members resembling outer portions of crowns of natural teeth with each of said cap members producing a new desired occlusal scheme and morphology which differs from the person's natural occlusal scheme and morphology, bonding each of said overlay cap members to said person's natural unaltered teeth, and providing spaces between adjacent overlay cap members to permit access through said spaces to the interdental spaces between said person's natural teeth on which said cap members are bonded.

* * * * *

UNITED STATES PATENT AND TRADEMARK OFFICE
CERTIFICATE OF CORRECTION

PATENT NO. : 4,710,127

DATED : December 1, 1987

INVENTOR(S) : William D. Bellavia and William Missert

It is certified that error appears in the above-identified patent and that said Letters Patent is hereby corrected as shown below:

Column 1, line 6, delete ", division,".

Column 1, line 50, after "to" delete the comma; and change "persons" to --person's--.

Column 6, line 15 (claim 2), delete "said person's" and after "bonding" (second occurrence) insert --said person's--.

Column 7, line 54 (claim 14), change "separated" to --separate--.

Signed and Sealed this

Tenth Day of May, 1988

Attest:

DONALD J. QUIGG

*Attesting Officer*    Commissioner of Patents and Trademarks